United States Patent
Dodson

(10) Patent No.: US 9,161,745 B2
(45) Date of Patent: Oct. 20, 2015

(54) MODULAR RETRACTOR AND RELATED METHOD

(71) Applicant: Mark A. Dodson, Alexandria, LA (US)

(72) Inventor: Mark A. Dodson, Alexandria, LA (US)

( * ) Notice: Subject to any disclaimer, the term of this patent is extended or adjusted under 35 U.S.C. 154(b) by 0 days.

(21) Appl. No.: 14/056,452

(22) Filed: Oct. 17, 2013

(65) Prior Publication Data

US 2014/0073857 A1 Mar. 13, 2014

Related U.S. Application Data

(63) Continuation of application No. PCT/US2012/058998, filed on Oct. 5, 2012.

(60) Provisional application No. 61/543,535, filed on Oct. 5, 2011.

(51) Int. Cl.
*A61B 17/02* (2006.01)
*A61B 1/32* (2006.01)
*A61B 17/00* (2006.01)

(52) U.S. Cl.
CPC ............... *A61B 17/0206* (2013.01); *A61B 1/32* (2013.01); *A61B 2017/00464* (2013.01)

(58) Field of Classification Search
CPC ............... A61B 17/02; A61B 17/0206; A61B 17/0218; A61B 17/0293
USPC ......... 600/201, 210, 213, 215, 218, 219, 222, 600/226
See application file for complete search history.

(56) References Cited

U.S. PATENT DOCUMENTS

| | | | | |
|---|---|---|---|---|
| 1,706,500 A | * | 3/1929 | Smith | 600/232 |
| 2,586,488 A | * | 2/1952 | Smith | 600/233 |
| 2,594,086 A | * | 4/1952 | Smith | 600/228 |
| 3,038,468 A | * | 6/1962 | Raeuchle | 600/233 |
| 3,070,088 A | * | 12/1962 | Brahos | 600/234 |
| 3,384,077 A | * | 5/1968 | Gauthier | 600/234 |
| 3,509,873 A | * | 5/1970 | Karlin et al. | 600/226 |
| 3,997,138 A | | 12/1976 | Crock et al. | |
| 3,998,217 A | * | 12/1976 | Trumbull et al. | 600/233 |
| 4,263,899 A | * | 4/1981 | Burgin | 600/213 |
| 4,502,485 A | * | 3/1985 | Burgin | 606/191 |
| 4,702,230 A | | 10/1987 | Pelta | |
| 4,829,985 A | * | 5/1989 | Couetil | 600/232 |

(Continued)

FOREIGN PATENT DOCUMENTS

DE 19542116 A1 5/1997
EP 2138122 A1 12/2009

(Continued)

*Primary Examiner* — Michael T Schaper
*Assistant Examiner* — Amy Sipp
(74) *Attorney, Agent, or Firm* — McGlinchey Stafford; R. Andrew Patty, II

(57) ABSTRACT

A retractor assembly for positioning tissue during a surgical procedure, having two opposing arms disposed adjacent to one another and sized and configured to be urged substantially laterally away from one another during actuation of the retractor assembly into an open position, and one or more posts, each post being connected to, or integral with, and extending radially outwardly from a respective one of the opposing arms, each of the one or more posts having a length sufficient so that each of the one or more posts will extend through a respective aperture defined by a modular component to be detachably attached to the respective one of the opposing arms. Related methods of positioning tissue during surgery are also described.

13 Claims, 6 Drawing Sheets

(56) References Cited

U.S. PATENT DOCUMENTS

| | | | |
|---|---|---|---|
| 4,887,596 A | 12/1989 | Sherman | |
| 5,052,373 A * | 10/1991 | Michelson | 600/217 |
| 5,067,477 A * | 11/1991 | Santangelo | 600/222 |
| 5,129,388 A | 7/1992 | Vignaud et al. | |
| 5,299,563 A * | 4/1994 | Seton | 600/215 |
| 5,330,473 A | 7/1994 | Howland | |
| D361,381 S * | 8/1995 | Koros et al. | D24/135 |
| 5,487,744 A | 1/1996 | Howland | |
| 5,520,689 A | 5/1996 | Schlapfer et al. | |
| 5,643,260 A | 7/1997 | Doherty | |
| 5,665,089 A | 9/1997 | Dall et al. | |
| 5,779,629 A * | 7/1998 | Hohlen | 600/233 |
| 5,795,291 A * | 8/1998 | Koros et al. | 600/232 |
| 5,893,831 A * | 4/1999 | Koros et al. | 600/232 |
| 5,944,658 A * | 8/1999 | Koros et al. | 600/232 |
| 5,967,974 A * | 10/1999 | Nicholas et al. | 600/233 |
| 5,984,867 A * | 11/1999 | Deckman et al. | 600/232 |
| 6,010,535 A | 1/2000 | Shah | |
| 6,022,350 A | 2/2000 | Ganem | |
| 6,030,340 A * | 2/2000 | Maffei et al. | 600/233 |
| 6,053,921 A | 4/2000 | Wagner et al. | |
| 6,063,090 A | 5/2000 | Schlapfer | |
| 6,090,111 A | 7/2000 | Nichols | |
| 6,196,969 B1 | 3/2001 | Bester et al. | |
| 6,206,879 B1 | 3/2001 | Marnay et al. | |
| 6,224,598 B1 | 5/2001 | Jackson | |
| 6,258,090 B1 | 7/2001 | Jackson | |
| 6,296,643 B1 | 10/2001 | Hopf et al. | |
| 6,368,320 B1 | 4/2002 | Le Couedic et al. | |
| 6,371,911 B1 * | 4/2002 | Hossain et al. | 600/232 |
| 6,423,065 B2 | 7/2002 | Ferree | |
| 6,440,064 B1 * | 8/2002 | Rehm | 600/232 |
| 6,443,953 B1 | 9/2002 | Perra et al. | |
| 6,454,768 B1 | 9/2002 | Jackson | |
| 6,464,634 B1 * | 10/2002 | Fraser | 600/233 |
| 6,488,683 B2 | 12/2002 | Lieberman | |
| 6,540,748 B2 | 4/2003 | Lombardo | |
| 6,540,749 B2 | 4/2003 | Schafer et al. | |
| 6,572,541 B1 * | 6/2003 | Petersvik | 600/233 |
| 6,616,669 B2 | 9/2003 | Ogilvie et al. | |
| 6,656,185 B2 | 12/2003 | Gleason et al. | |
| 6,659,945 B2 * | 12/2003 | Ball et al. | 600/233 |
| 6,689,137 B2 | 2/2004 | Reed | |
| 6,712,795 B1 * | 3/2004 | Cohen | 604/233 |
| 6,726,687 B2 | 4/2004 | Jackson | |
| 6,783,527 B2 | 8/2004 | Drewry et al. | |
| 6,887,198 B2 * | 5/2005 | Phillips et al. | 600/228 |
| 7,018,378 B2 | 3/2006 | Biedermann et al. | |
| D522,140 S * | 5/2006 | Stalcup et al. | D24/135 |
| 7,056,287 B2 * | 6/2006 | Taylor et al. | 600/210 |
| 7,137,949 B2 * | 11/2006 | Scirica et al. | 600/229 |
| 7,250,052 B2 | 7/2007 | Landry et al. | |
| 7,306,603 B2 | 12/2007 | Boehm, Jr. et al. | |
| 7,344,537 B1 | 3/2008 | Mueller | |
| 7,503,918 B2 | 3/2009 | Baccelli et al. | |
| 7,611,518 B2 | 11/2009 | Walder et al. | |
| 7,678,139 B2 | 3/2010 | Garamszegi et al. | |
| 7,686,834 B2 | 3/2010 | Saint Martin | |
| 7,691,129 B2 | 4/2010 | Felix | |
| 7,699,876 B2 | 4/2010 | Barry et al. | |
| 7,708,762 B2 | 5/2010 | McCarthy et al. | |
| 7,744,635 B2 | 6/2010 | Sweeney et al. | |
| 7,766,946 B2 | 8/2010 | Bailly | |
| 7,780,706 B2 | 8/2010 | Marino et al. | |
| 7,833,251 B1 | 11/2010 | Ahlgren et al. | |
| 7,842,074 B2 | 11/2010 | Abdou | |
| 7,846,187 B2 | 12/2010 | Jackson | |
| 7,901,437 B2 | 3/2011 | Jackson | |
| 7,931,676 B2 | 4/2011 | Veldman et al. | |
| 7,935,135 B2 | 5/2011 | Mujwid | |
| 7,942,907 B2 | 5/2011 | Richelsoph | |
| 7,942,909 B2 | 5/2011 | Hammill, Sr. et al. | |
| 7,951,172 B2 | 5/2011 | Chao et al. | |
| 7,967,848 B2 | 6/2011 | Abdelgany | |
| 7,967,850 B2 | 6/2011 | Jackson | |
| 7,976,463 B2 * | 7/2011 | Dewey et al. | 600/210 |
| 7,988,710 B2 | 8/2011 | Jahng et al. | |
| 8,012,177 B2 | 9/2011 | Jackson | |
| 8,016,862 B2 | 9/2011 | Felix et al. | |
| 8,029,547 B2 | 10/2011 | Veldman et al. | |
| 8,048,109 B2 * | 11/2011 | Garcia-Bengochea | 606/213 |
| 8,048,112 B2 | 11/2011 | Suzuki et al. | |
| 8,062,340 B2 | 11/2011 | Berrevoets et al. | |
| 8,092,500 B2 | 1/2012 | Jackson | |
| 8,177,810 B2 | 5/2012 | Ferree | |
| 8,226,554 B2 * | 7/2012 | McBride et al. | 600/219 |
| D671,641 S | 11/2012 | Fritzinger | |
| 8,523,770 B2 * | 9/2013 | McLoughlin | 600/233 |
| 8,808,176 B2 | 8/2014 | Menendez et al. | |
| 2002/0138077 A1 | 9/2002 | Ferree | |
| 2002/0188297 A1 | 12/2002 | Dakin et al. | |
| 2003/0055319 A1* | 3/2003 | Chang | 600/210 |
| 2004/0242969 A1* | 12/2004 | Sherts et al. | 600/231 |
| 2005/0171537 A1 | 8/2005 | Mazel et al. | |
| 2005/0215865 A1 | 9/2005 | LeVahn et al. | |
| 2005/0267470 A1 | 12/2005 | McBride | |
| 2006/0135958 A1 | 6/2006 | Marissen et al. | |
| 2007/0073111 A1* | 3/2007 | Bass | 600/215 |
| 2007/0093201 A1 | 4/2007 | Freudiger | |
| 2007/0122764 A1 | 5/2007 | Balfour et al. | |
| 2009/0030466 A1 | 1/2009 | Strauss | |
| 2009/0093684 A1 | 4/2009 | Schorer | |
| 2009/0105547 A1* | 4/2009 | Vayser et al. | 600/228 |
| 2009/0149887 A1 | 6/2009 | Schlaepfer et al. | |
| 2009/0164016 A1 | 6/2009 | Georgy et al. | |
| 2009/0171392 A1 | 7/2009 | Garcia-Bengochea et al. | |
| 2009/0203967 A1 | 8/2009 | Branch et al. | |
| 2009/0203969 A1* | 8/2009 | Cohen et al. | 600/245 |
| 2009/0248088 A1 | 10/2009 | Biedermann | |
| 2009/0264933 A1 | 10/2009 | Carls et al. | |
| 2009/0292317 A1 | 11/2009 | Belliard | |
| 2010/0010540 A1 | 1/2010 | Park | |
| 2010/0063546 A1 | 3/2010 | Miller et al. | |
| 2010/0087865 A1 | 4/2010 | Biedermann et al. | |
| 2010/0160975 A1 | 6/2010 | Biedermann et al. | |
| 2010/0160976 A1 | 6/2010 | Biedermann et al. | |
| 2010/0234901 A1 | 9/2010 | Levy | |
| 2010/0241175 A1 | 9/2010 | Walker et al. | |
| 2010/0262185 A1 | 10/2010 | Gelfand et al. | |
| 2010/0274295 A1 | 10/2010 | Carls et al. | |
| 2011/0066188 A1 | 3/2011 | Seme et al. | |
| 2011/0112581 A1 | 5/2011 | Clement | |
| 2011/0144699 A1 | 6/2011 | Fallin et al. | |
| 2011/0245875 A1 | 10/2011 | Karim | |
| 2011/0301644 A1 | 12/2011 | Belliard | |
| 2012/0035671 A1 | 2/2012 | Hodge et al. | |
| 2012/0130373 A1 | 5/2012 | Larroque-Lahitette | |
| 2014/0135584 A1* | 5/2014 | Lee et al. | 600/202 |

FOREIGN PATENT DOCUMENTS

| | | |
|---|---|---|
| EP | 2465457 A1 | 6/2012 |
| FR | 2734471 A1 | 11/1996 |
| WO | WO 9532676 A1 | 12/1995 |
| WO | WO 03041599 A1 | 5/2003 |
| WO | WO 2006004367 A1 | 1/2006 |
| WO | WO 2008061802 A1 | 5/2008 |
| WO | WO 2011051316 A2 | 5/2011 |
| WO | WO 0154599 A1 | 8/2011 |
| WO | WO 2013052827 A1 | 4/2013 |

* cited by examiner ated # MODULAR RETRACTOR AND RELATED METHOD

REFERENCE TO RELATED APPLICATIONS

This application is a continuation of copending and commonly-owned International Patent Application No. PCT/US2012/058998, filed on Oct. 5, 2012, which claims priority to commonly owned U.S. Provisional Patent Appl. No. 61/543,535, filed on Oct. 5, 2011, the disclosures of which are incorporated herein by reference.

TECHNICAL FIELD

This invention pertains to the technical field of medical devices, namely retractors for use in orthopedic and other surgical procedures.

THE INVENTION

Retractors and retractor assemblies are commonly used to draw back and retain tissue from a surgical site. Many retractor designs are competent at retaining open an incision, but are less useful in isolating bone or other internal target areas while dependably retracting deeper tissue below the skin and below the shallow tissues which surround the incision. Conventional retractors, even those of the self-retaining type for example, often require adjustment or manipulation by a surgical assistant when retraction and/or isolation of deeper tissues might be necessary during a surgeon's work. Thus, a need persists for retractor apparatus with improved ease of use, efficiency of design and effectiveness at tissue retraction and target isolation within the surgical field.

The present invention addresses this need by providing, in one aspect, a retractor assembly for positioning tissue during a surgical procedure, the assembly comprising:
  two opposing arms disposed adjacent to one another and sized and configured to be urged substantially laterally away from one another during actuation of the retractor assembly into an open position,
  one or more posts, each being connected to, or integral with, and extending radially outwardly from a respective one of the opposing arms, each of the one or more posts having a length sufficient so that each of the one or more posts will extend through a respective aperture defined by a modular component to be detachably attached to the respective one of the opposing arms.

It can be preferred, in certain aspects of the invention, that at least one of the one or more posts is non-circular (e.g., square, rectangular, hexagonal, etc.) when viewed in cross-section through a longitudinal axis thereof. The retractor assembly may further comprise a plurality of posts extending from each of the opposing arms.

The retractor assembly may further comprise at least one modular component, which component defines one or more apertures, each aperture being sized and configured to mate with a respective one of the posts to thereby detachably attach the modular component to the arm from which the respective one of the posts extends. In some aspects of the invention, each aperture defined by the modular component is sized and configured to mate with the respective one of the posts so as to inhibit rotational motion of the modular component about the longitudinal axis of the respective one of the posts. The modular component further may comprise a planar member forming one or more flanges. In such cases, preferably the one or more flanges is sized to extend into the surgical field when the modular component is detachably attached to the respective one of the opposing arms and the retractor assembly is deployed in the open position during use. In one particular embodiment of the invention, the modular component comprises a Hohmann retractor.

In another aspect of this invention, there is provided a method of positioning tissue during a surgical procedure. The method comprises
  detachably attaching a modular component to each of two opposing arms of a self-retaining retractor assembly, by at least mating respectively one or more apertures defined by a respective one of the modular components with one or more posts, the one or more posts being connected to or integral with and extending radially outwardly from a respective one of the opposing arms;
  disposing at least a portion of the modular components of each of the two opposing arms into a surgical field; and
  urging the opposing arms laterally away from one another and into an open position so as to place the modular components into contact with and to position the tissue during the surgical procedure.

In at least some embodiments of the invention, the method further comprises temporarily retaining the modular components in the opened position by temporarily retaining the opposing arms in the opened position. In one particular aspect of the invention, the opposing arms are pivotally connected to one another, and together define a ratchet connection employed in temporarily retaining the opposing arms in the opened position.

These and other embodiments, features and advantages of the present invention will become even further apparent from the accompanying drawings, the following detailed description and the appended claims.

FURTHER DETAILED DESCRIPTION OF THE INVENTION

With surprising simplicity, the retractor assembly of this invention, in at least one of its embodiments, enables facile retraction of tissue from a surgical field, even when an assistant is not readily available or only a single hand is free to manipulate the retractor. Select embodiments of the invention also provide the convenience of a modular configuration, permitting of variations in the components configured to be engaged by the posts extending substantially laterally from the opposing retractor arms. In this way, the same main retractor assembly of opposed arms and associated lateral posts may be mated selectively with a specific pair or set of the same or different modular components, selected as best adapted for use in the given surgical procedure at hand.

The one or more posts extend substantially laterally from the opposing retractor arms in that they may extend within the same general plane occupied by the opposing arms, or may have a longitudinal axis which is disposed at an angle relative to the general plane occupied by the opposing arms. In some embodiments of the invention, it may be desirable, for example, for each post to extend laterally and slightly upward from its associated opposing arm at an angle of, e.g., at least 5 degrees or more from a plane generally occupied by the adjacent opposing arms of the assembly. Such angular disposing of the one or more posts can serve to at least ensure the modular components of the assembly remain mated to their respective one or more post during use of the retractor assembly.

Figure 1:
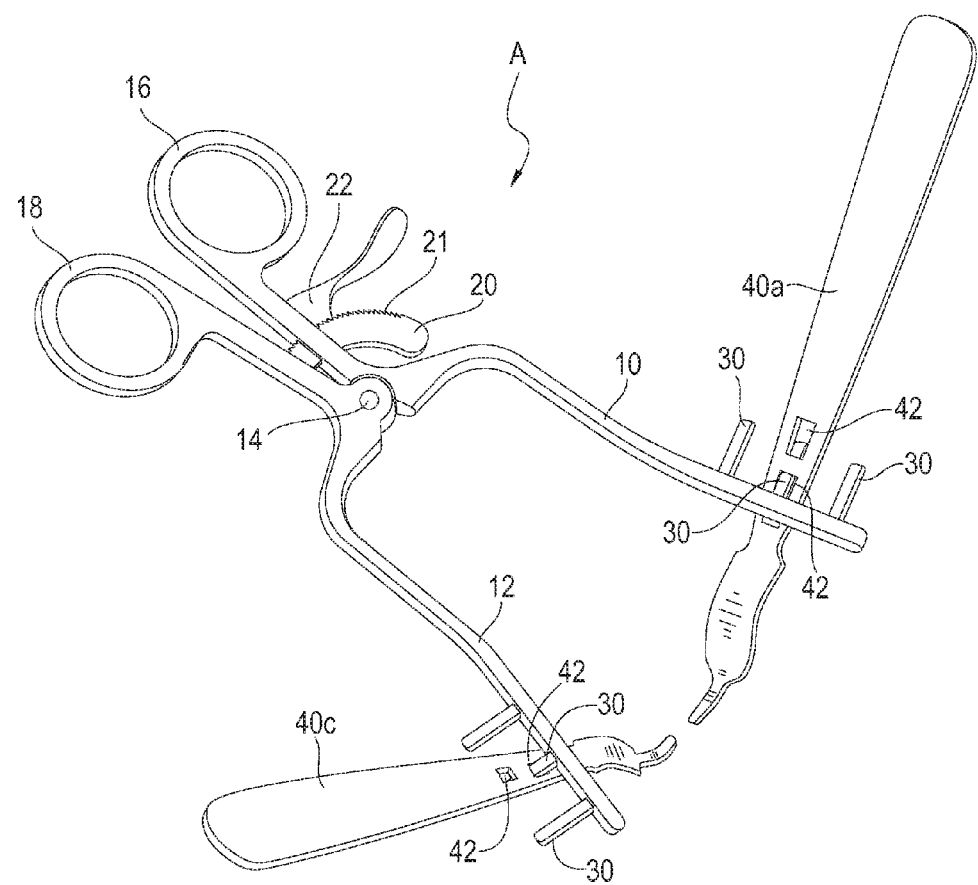
FIG. 1 is an elevated view in perspective of one embodiment of the present invention.

Turning now to the figures, it will be seen that a particular embodiment of this invention is illustrated by the self-retaining retractor assembly A shown in FIG. 1. Assembly A comprises two opposing retractor arms 10 and 12 disposed adjacent to one another and sized and configured to be urged substantially laterally away from one another during actuation of the retractor assembly into an open position. In the illustrated embodiment, such sizing and configuration is provided by pivotally connecting arms 10 and 12 to one another at pin 14, arms 10 and 12 forming thumb and finger loops 16 and 18, respectively, and further forming a ratchet component itself formed by a curved flange 20 defining ratchet teeth 21 and a spring-biased ratchet claw 22. Teeth 21 and claw 22 mate with one another to releasably retain arms 10 and 12 in an open position (i.e., a position which will urge the surgical field-engaging portions of the retractor arms away from one another) when loops 16 and 18 of arms 10 and 12 are brought together manually. Biasing claw 22 to release from teeth 21 when desired will free the opposing arms 10 and 12 so that they may be placed in a closed position when loops 16 and 18 are separated. At the opposing ends of arms 10 and 12, there are provided a plurality of posts 30 each being connected to, or integral with, and extending radially outwardly from a respective one of the opposing arms 10 and 12. As illustrated, one of each set of three posts 30 extending from each of arms 10 and 12 is mated with a modular component in the form of a Hohmann retractor 40a and 40c, respectively. Each of retractors 40a and 40c form at least one, and as illustrated at least two, shaped apertures 42, sized and configured to tightly mate in a lock-and-key fashion with a respect one of the posts 30. In this context, to tightly mate means that the clearance between an inner wall of at least one (and preferably each) aperture 42 and at least one lateral side of its associated post 30 is sufficiently small so as to allow for less than 15 degrees of rotation of the modular component about the longitudinal axis of the post, thereby providing a relatively snug mating of the post 30 with its respective aperture 42 to prevent retractors 40a and 40c excessive movement about the longitudinal axis of associated post 30, without being so snug that retractors 40a and 40c cannot be readily de-coupled from the associated posts 30 manually. This fit between each post and its associated modular component aperture is particularly important when the modular component is configured to detachably attach to a respective arm by mating only one aperture with one post when installed in the assembly. As illustrated in FIG. 1, the Hohmann retractors 40a and 40c further define a series of two or more apertures 42 in order to provide options to the user to adjust the depth or other position of the modular component attachment, in this case the retractors 40a and 40c. When multiple apertures are defined by the modular component(s), the apertures in a given modular component may be the same shape or different shapes.

Figure 8:
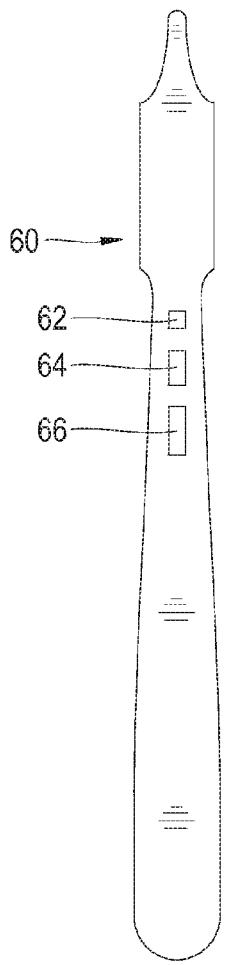
FIG. 8 is a top view of a Hohmann-type retractor component in accordance with another embodiment of the invention.
Figure 9:
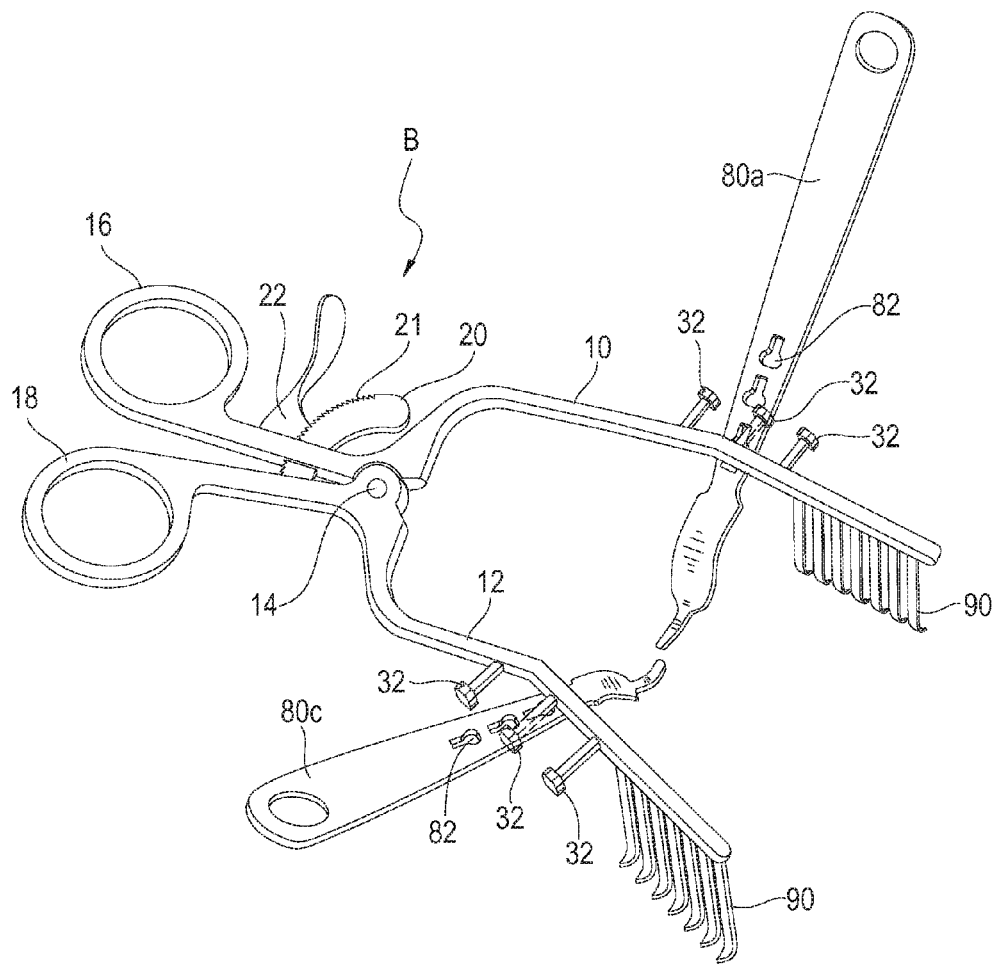
FIG. 9 is an elevated view in perspective of a retractor assembly in accordance with yet another embodiment of the invention.
Figure 10:
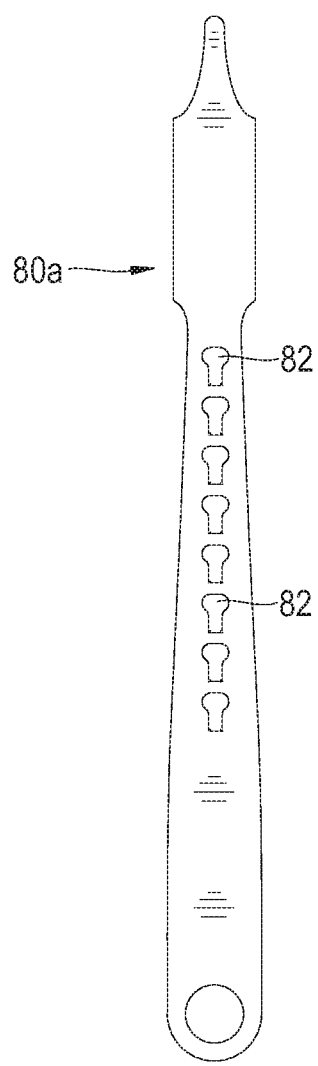
FIG. 10 is a top view of the modified Hohmann-type retractor component of the retractor assembly illustrated in FIG. 9.

For example, as seen in FIG. 8, in order to provide options for tilting the Hohmann retractor 60 (which is similar to retractor 40a and 40c of FIG. 1) laterally at different depths and at different angles from perpendicular during use, retractor 60 defines three different apertures 62, 64 and 66, and the rectangular shape of aperture 66 is longer than aperture 64, which is longer again than aperture 62, so that the user can vary the angular tilt of the retractor component by employing the appropriate aperture for a preferred angle. The longer rectangular apertures 64 and 66 permit and upper portion of retractor 60 to tilt from perpendicular laterally (as shown for retractors 40a and 40c in FIG. 1) at greater respective degrees as compared to aperture 62, while still providing sufficiently small lateral post clearance to prevent excessive rotational motion of retractor 60 about the longitudinal axis of post 30 when employed in the assembly of this invention. FIGS. 9 and 10 illustrate alternative Hohmann retractors 80a and 80c, each also defining multiple shaped apertures 82 (described in greater detail below) along the length of the retractor, in order to provide options for tilting laterally at different depths and at different angles from perpendicular during use.

Figure 2:
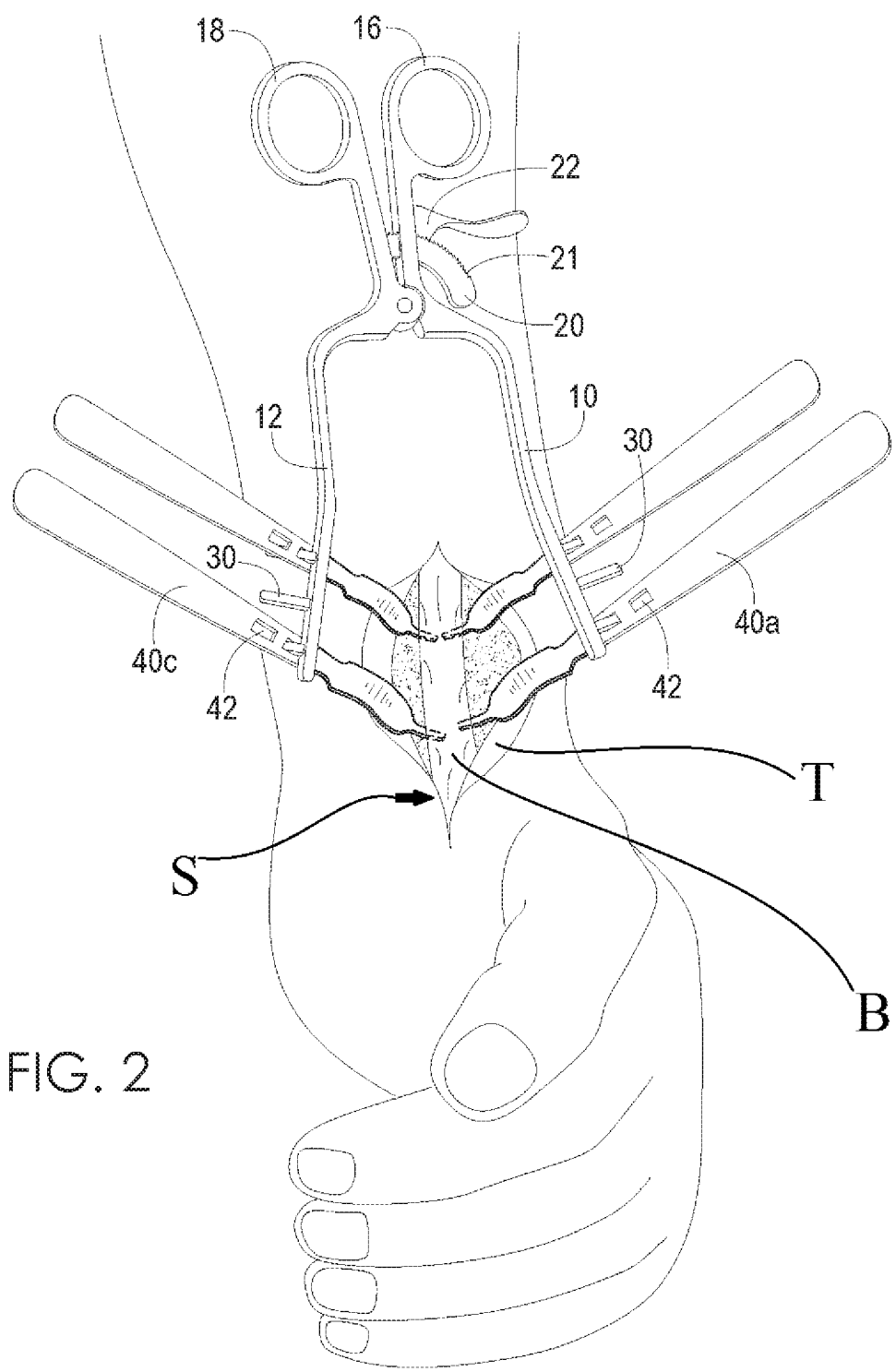
FIG. 2 is an elevated view in perspective of the embodiment of FIG. 1, shown in use to retract a surgical site on a human arm, isolating bone within that site.

In FIG. 2, the assembly of FIG. 1 is illustrated in use, but with two pairs of Hohmann retractors 40a and 40b, and 40c and 40d, mated to respective posts 30. The Hohmann retractors illustrated extend into a surgical site S and extend under a bone B. Assembly A is in an open position to retain tissue T away from bone B during the procedure and to further isolate bone B. Through the use of a plurality of posts 30 and the two pair of retractors 40a, 40b, and 40c, 40d, a well-retained surgical field can be obtained with effective isolation of bone B with one manual actuation of the self-retaining retractor assembly's rachet component by manually bringing together loops 16 and 18 once the Hohmann retractors 40a, 40b, 40c and 40d are positioned into the field S and adjacent bone B.

Figure 7:
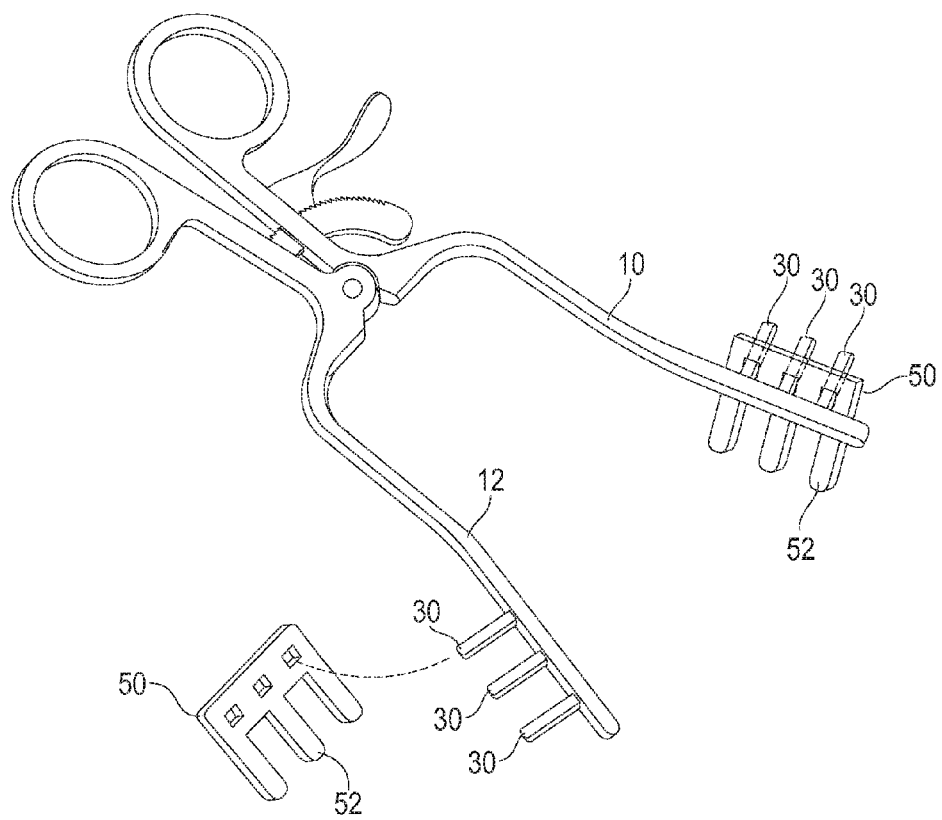
FIG. 7 is an elevated view in perspective of a portion of the retractor assembly of FIG. 1, substituting modular attachments in accordance with FIG. 4 for the Hohmann-type retractor components shown in FIG. 1.

FIG. 2 further illustrates the method of this invention, for positioning tissue during a surgical procedure. With reference to FIG. 2 and FIG. 7, it can be seen that, in practicing the method, one detachably attaches a modular component (e.g., the Hohmann retractors of FIG. 2) to each of two opposing arms 10 and 12 of the self-retaining retractor assembly, by at least mating respectively one or more apertures 42 defined by a respective one of the modular components (Hohmann retractors) with one or more posts 30, the one or more posts being connected to or integral with and extending radially outwardly from a respective one of the opposing arms 10 or 12. The method further comprises disposing at least a portion of the modular components of each of the two opposing arms 10 and 12 into the surgical field, and urging the opposing arms 10 and 12 laterally away from one another and into an open position so as to place the modular components into contact with, and to position, the tissue during the surgical procedure. Such urging is typically, but not necessarily, carried out manually by the user. The method may further comprise temporarily retaining the modular components in the opened position by temporarily retaining the opposing arms 10 and 12 in the opened position. As illustrated, this is carried out through the use of the ratchet component of the assembly and a pivoting connection of the opposing arms, but of course other means of carrying out such retention can be envisioned once the feature of this invention are known. For example, fasteners such as screws, bolts and nut configurations, and the like, or clamps or other mechanical components could be employed to controllably and temporarily retain the opposing arms in the opened position and/or vary the space between those opposing arms during use.

The present invention is modular in that alternative or additional modular components can be provided to mate with the substantially laterally extending posts of the opposed arms of the retractor assembly. Thus, for example, as seen in FIGS. 3, 4, 5 and 6, a wide variety of modular components, in addition to or as an alternative to a Hohmann retractor component, can be envisioned for use as a part of the assembly of the invention. As seen in those figures, the modular component comprises a plate 50 which forms one or more flanges 52 and defines one and one or more apertures 42, and the plate 50 can vary widely in its shape and configuration, in order to suit a particular surgical need or procedure.

Figure 3:
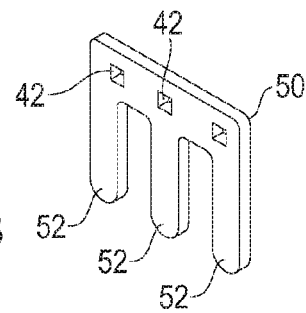
FIG. 3 is an elevated view in perspective of a modular attachment in accordance with one embodiment of this invention, which attachment could be used with the retractor assembly of FIG. 1.
Figure 4:
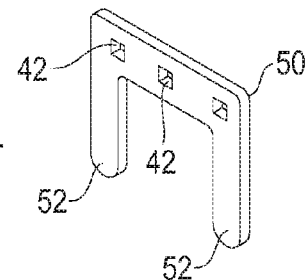
FIG. 4 is an elevated view in perspective of another modular attachment in accordance with one embodiment of this invention, which attachment could be used with the retractor assembly of FIG. 1.
Figure 5:
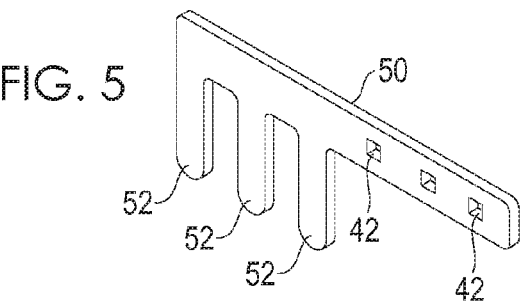
FIG. 5 is an elevated view in perspective of another modular attachment in accordance with one embodiment of this invention, which attachment could be used with the retractor assembly of FIG. 1.
Figure 6:
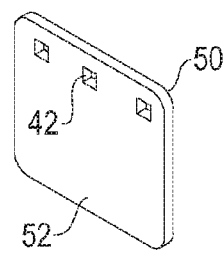
FIG. 6 is an elevated view in perspective of another modular attachment in accordance with one embodiment of this invention, which attachment could be used with the retractor assembly of FIG. 1.

FIG. 7 further illustrates another embodiment of the invention, and the mating of a modular component 50 in accordance with FIG. 3 with retractor assembly arms 10 and 12.

In another aspect of the invention illustrated with reference to FIGS. 9 and 10, there is provided a self-retaining retractor assembly B with several features similar to those of the assembly A of FIG. 1. Assembly B further provides Hohmann retractor components 80a and 80c which define key-hole type apertures 82 for receiving and mating with modified posts 32 which are connected to or integral with and extending radially outwardly from a respective one of the opposing arms 10 or 12. Posts 32 are each modified from the posts 30 illustrated in the assembly of FIG. 1, in that posts 32 each define an enlarged section or head at the free end, the enlarged section being sized and configured to be received through a mating portion of a respective shaped aperture 82. Once the enlarged portion of each post 32 has been received through its respective aperture 82, retractor 80a or 80c can be positioned so that the respective narrower portion of aperture 82 mate with the respective narrower section of post 32, as previously illustrated and described for posts 30 and aperture 42 of FIG. 2. This can reduce rotational movement of the respective Hohmann-type retractor component, while the enlarged portion of each post 32 will inhibit unintentional displacement or removal of the respective Hohmann-type retractor component from its associated post. It should be appreciated from this disclosure by those of skill in the art, that the particular shapes of the key-hole type apertures and mating posts (including the associated enlarged head portion of each) can vary from those illustrated while remaining within the spirit and scope of the invention.

As illustrated in FIG. 9, to illustrate another alternative design, assembly B further includes a pair of retention paddles, each in the form of a plurality of adjacent curved flanges 90, affixed to and extending in the same general direction from respective ends of the two opposing arms 10 and 12 of assembly B. While as illustrated the retention paddles are integral with the opposing arms, it will be appreciated that these retention elements also may be modular in design, so that either or each is configured to be readily attached and detached to its respective opposing arm.

Those of skill in the art will now appreciate that a wide variety of modular components could be sized and configured for use in the retractor assembly of this invention for use in many different types of surgical procedures. Moreover, a variety of sizes and configurations may be employed to provide a mechanism for bringing together and urging apart and retaining in place the opposing arms of the retractor assemblies of this invention, and those of skill in this art will now appreciate that the specific self-retaining mechanism illustrated in the accompanying figures is not the only configuration which could be employed to effectuate the positioning and retention of the opposing arms and associated modular components during use. Likewise, the number of apertures defined by the modular components, the number of laterally extending posts and their specific length and lateral position relative to the associated opposing arm, as well as the size and the shape and the number of modular components employed, can vary to accommodate different but desirable design criteria for a given retractor assembly of the invention, or to better facilitate retraction in a given surgical procedure. Likewise, the length of the opposing arms can be varied to increase the retraction. Due to the modular design of the assembly of this invention, various modular component attachments can be applied alone or in combination. One type can be used on one arm and a different type on the other. The design also allows for the addition or removal of the modular component attachments during surgical procedure. The modular components and other parts of the retractor assembly of this invention can be fabricated of any surgical grade material suitable for use in conventional retractor assemblies.

The foregoing description of various embodiments of the present invention are illustrative only, and are not to be construed as limiting the scope of the invention. Many varying and different embodiments of the invention not specifically detailed herein nevertheless may be envisioned easily by those of skill in the art who have the benefit of the present disclosure, and therefore the scope of the invention is properly defined by the appended claims and equivalents thereof permitted as a matter of law.

The invention claimed is:

1. A retractor assembly for positioning tissue during a surgical procedure, the assembly comprising:
   two opposing arms disposed adjacent to one another and sized and configured to be urged substantially laterally away from one another during actuation of the retractor assembly into an open position,
   one or more posts, each being connected to, or integral with, and extending radially outwardly from a respective one of the opposing arms and away from a space defined between the arms, and
   at least two modular components,
   each of the one or more posts having a length sufficient so that each of the one or more posts will extend through a respective rectangular aperture defined by a respective one of the modular components to be detachably attached to the respective one of the opposing arms, the rectangular aperture being sized and configured to enable the respective modular component to tilt laterally relative to its respective post while being detachably attached to the respective one of the opposing arms and engaged with tissue during use of the retractor assembly, each rectangular aperture being sized and configured to mate with a respective one of the posts to thereby detachably attach the modular component to the arm from which the respective one of the posts extends.

2. A retractor assembly according to claim 1, wherein at least one of the one or more posts is non-circular when viewed in cross-section through a longitudinal axis thereof.

3. A retractor assembly according to claim 1, further comprising a plurality of posts extending from each of the opposing arms.

4. A retractor assembly according to claim 3, wherein at least one of the one or more posts is non-circular when viewed in cross-section through a longitudinal axis thereof.

5. A retractor assembly according to claim 1, wherein at least one of the two modular components defines two or more rectangular apertures along its length, each rectangular aperture being sized and configured to mate with a respective one of the posts to thereby detachably attach the modular component to the arm from which the respective one of the posts extends.

6. A retractor assembly according to claim 5, wherein each rectangular aperture defined by the modular component is sized and configured to mate with the respective one of the posts so as to inhibit rotational motion of the modular component about a longitudinal axis of the respective one of the posts.

7. A retractor assembly according to claim 6, wherein the modular component comprises a planar member forming one or more flanges.

8. A retractor assembly according to claim 7, wherein the one or more flanges are each sized to extend into a surgical field when the modular component is detachably attached to the respective one of the opposing arms and the refractor assembly is deployed in the open position during use.

9. A retractor assembly according to claim 5, wherein each of the modular components comprises an elongate blade forming two opposed faces and the respective rectangular aperture extends through the opposed faces of the respective one of the modular components.

10. A retractor assembly according to claim 9, wherein the two opposing arms are pivotally connected to one another.

11. A retractor assembly according to claim 1, wherein the tissue comprises bone.

12. A retractor assembly according to claim 1, wherein the two opposing arms are pivotally connected to one another.

13. A retractor assembly for positioning tissue during a surgical procedure, the assembly comprising:
    two opposing arms disposed adjacent to one another and pivotally connected to one another so as to be urged substantially laterally away from one another within a plane during pivoting actuation of the retractor assembly into an open position,
    one or more posts, each being connected to, or integral with, and extending radially outwardly from a respective one of the opposing arms in the plane and away from a space defined between the arms, and
    at least two modular components, each comprising a retractor blade forming two opposing faces,
    each of the one or more posts having a length sufficient so that each of the one or more posts will extend through a respective rectangular aperture, the aperture extending through the opposed faces of the respective one of the modular components to be detachably attached to the respective one of the opposing arms, the rectangular aperture being sized and configured to enable the respective modular component to tilt laterally relative to its respective post while being detachably attached to the respective one of the opposing arms and engaged with tissue during use of the retractor assembly, each rectangular aperture being sized and configured to mate with a respective one of the posts to thereby detachably attach the modular component to the arm from which the respective one of the posts extends.

* * * * *